United States Patent [19]

Tsavaris

[11] 4,128,833
[45] Dec. 5, 1978

[54] HOTWELL ALARM SYSTEM

[76] Inventor: Emmanuel J. Tsavaris, 28-33 Hobart St., Woodside, N.Y. 11377

[21] Appl. No.: 785,608

[22] Filed: Apr. 7, 1977

[51] Int. Cl.² .................. G08B 21/00; B01D 35/00; B01D 43/00
[52] U.S. Cl. ..................... 340/603; 210/95; 210/96 R; 210/521; 356/70
[58] Field of Search .............. 340/236, 239 R, 242; 250/564, 565, 573, 574, 575; 356/70, 103, 208; 73/61.1 R; 210/94, 95, 96 R, 221 R, DIG. 26, 521, 320

[56] References Cited

U.S. PATENT DOCUMENTS

| 974,025 | 10/1910 | Clark et al. | 210/95 |
|---|---|---|---|
| 1,166,802 | 1/1916 | Albert et al. | 210/320 X |
| 1,994,768 | 3/1935 | Holven et al. | 340/239 R UX |
| 2,562,181 | 7/1951 | Frommer | 250/574X |
| 2,631,511 | 3/1953 | Tuttle | 250/573 X |
| 2,692,528 | 10/1954 | Uhl | 210/94 X |
| 3,845,480 | 10/1974 | Steinberg | 340/236 |
| 3,939,072 | 2/1976 | LaForte | 210/96 R |

Primary Examiner—John W. Caldwell, Sr.
Assistant Examiner—Daniel Myer
Attorney, Agent, or Firm—Sydney B. Schlessel

[57] ABSTRACT

An alarm system for the detection of oil pollution in a feedwater system, comprising a housing having an inlet water line at one end and an outlet water line at the other end and formed with a series of internal, alternately disposed baffles adapted to retard water flow and forming passes thereinbetween, a light disposed in the floor of the housing before the first baffle with its beam directed to the roof of the housing, and an electric eye circuit disposed in the housing roof in registry with said beam, whereby dimming of the light beam by the introduction of oil in the water flowing inbetween activates an audible and visual alarm. Filter means are provided at the discharge end of the housing to remove sediment and particles passing through the housing.

8 Claims, 3 Drawing Figures

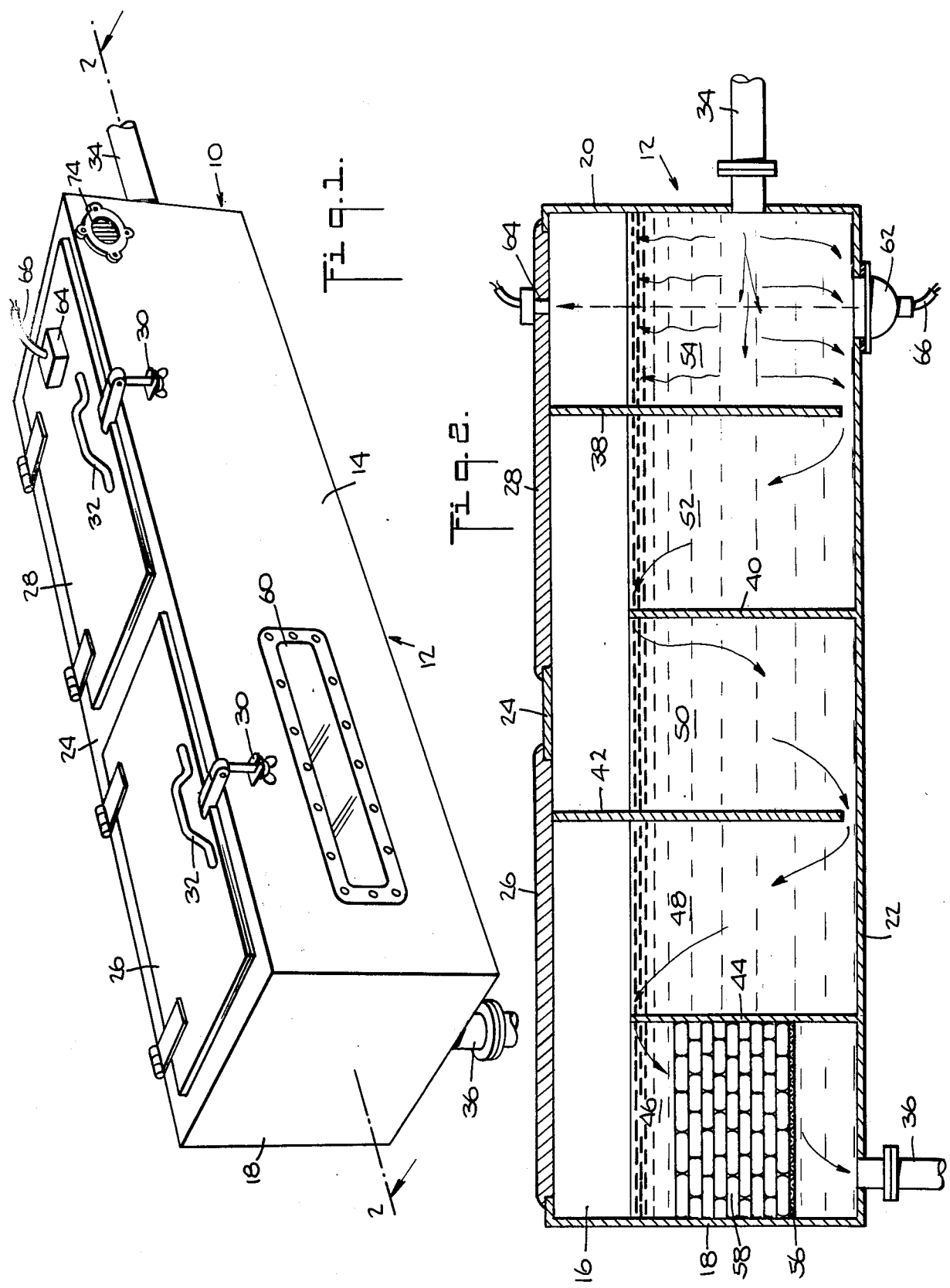

HOTWELL ALARM SYSTEM

BACKGROUND OF THE INVENTION (a) Field of the invention.

This invention relates to the field of pollution detection, and has for its objective the creation of an alarm system for ships and the like, whereby the accidental entry of oil or similar pollutants into the feedwater system and water lines leading to the ship's boilers is quickly detected and an alarm given, so that the crew members can act expeditiously to prevent such pollutants from reaching and damaging the boilers. It is also the object of this invention to provide a filtering system to filter the water before it reaches the boilers.

(b) Prior art.

As is well known in the art, leaks often develop in the fuel oil bunkers aboard ships, and the oil often finds its way into the feedwater systems, by seepage or otherwise. If not instantly detected and removed, the oil can be thus carried into the ship's boilers, thereby disabling the ship and causing great damage and destruction to the boilers and the boiler tubes. At present such detection is limited to visual examination of the feedwater lines by the crew as the water passes an inspection point on its way to the boilers. The disadvantages found in such procedure is the delegation of crew members for such purpose, the fact that the attention of the crew member may be distracted for a sufficient time to enable undetected oil to reach the boilers, and, further, that by the time the oil is detected and the flow stopped sufficient oil may have reached the boilers to cause damage. Various devices have heretofore been created for the detection of oil or a liquid of greater density in water, etc. by means of variations of reflection, as well as light responsiveness and light transmissions. However, none of such devices can be used for the purposes for which my invention was devised, nor can they be adapted for such functions.

BRIEF DESCRIPTION OF THE INVENTION

The aforementioned disadvantages are overcome by my invention, which provides an intermediate housing (which hereinafter will be designated as a "Hotwell") through which water coming from the ship's feedwater system is fed into an outlet line at the other end of the hotwell and leading to the boilers, the housing provided internally with a series of parallel, spaced, alternately-open baffles, forming passes thereinbetween to impede the natural flow of the water and thereby slow up the passage of oil, if any, carried by the water, with a photoelectric alarm system disposed within the first pass to quickly detect and warn of the presence of any oil pollutant coming into the hotwell, by the change in fluid density and transparency, together with a filtering means within the last pass, to filter and remove organic particles.

It is therefore the principal object of my invention to provide a hotwell alarm system whereby fuel oil leaking into the water lines is detected before it can reach and damage the ship's boilers.

A second important object of my invention lies in the provision of a hotwell alarm system whereby the advance of incidental oil in the ship's water lines is impeded without slackening the flow of water.

A third important object of my invention lies in the provision of a hotwell alarm system whereby the presence of even a small quantity of oil is detected within a matter of a few seconds.

A fourth important object of my invention lies in the provision of an alarm system as described herein, which is inexpensive to produce and simple to operate.

These and other salient objects, advantages and functional features of my invention will become more readily apparent from an examination of the following description, taken with the accompanying drawings, wherein:

BRIEF DESCRIPTION OF THE DRAWINGS

FIG. 1 is a perspective view of a preferred embodiment of my invention;

FIG. 2 is a cross-sectional view, taken on lines 2—2 of FIG.1; and

Similar reference characters designate similar parts throughout the different views.

DETAILED DESCRIPTION OF THE INVENTION

Figure 3:
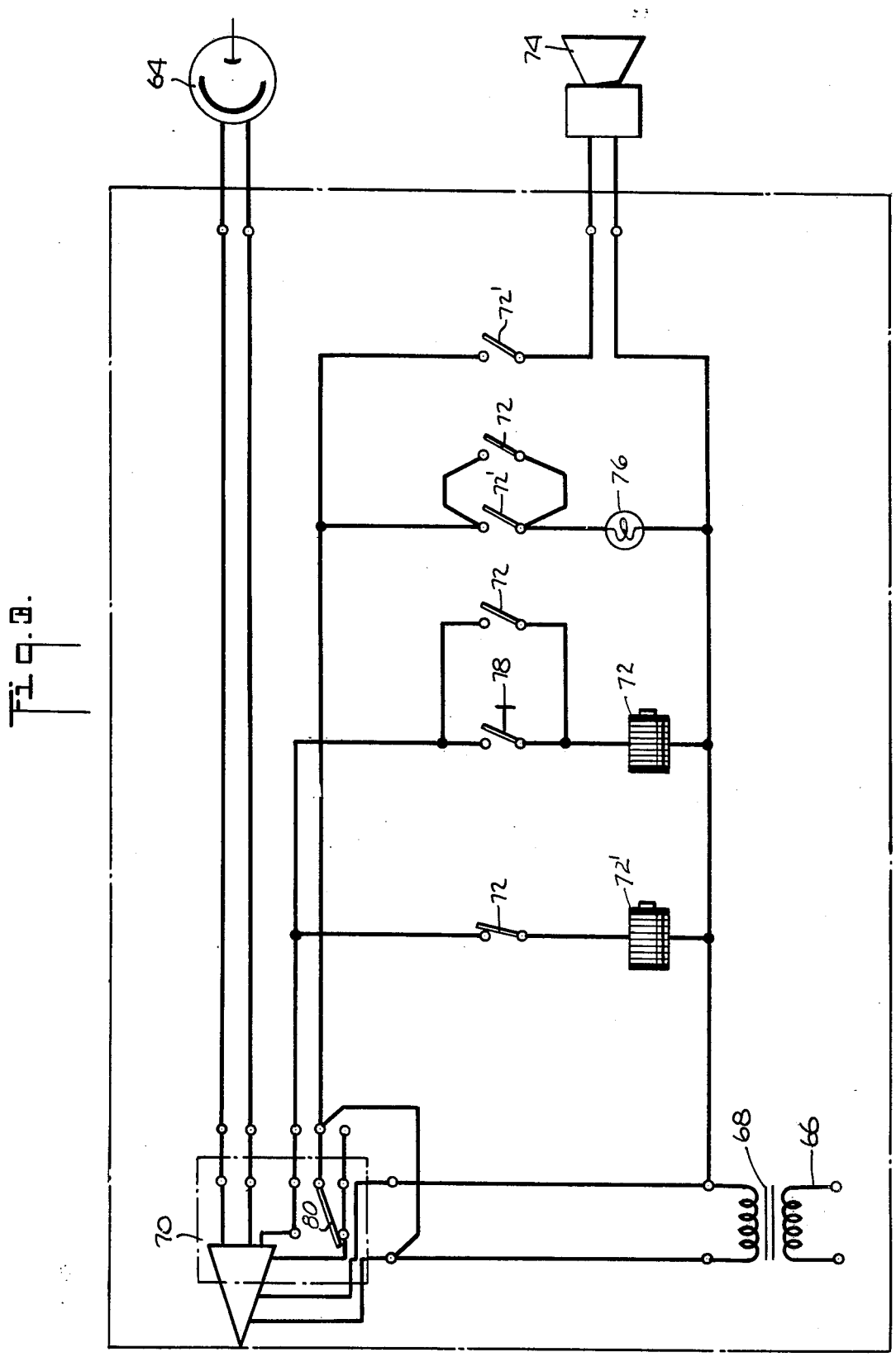
FIG. 3 is a diagrammatic illustration of a photoelectric circuit system incorporated therein.

Illustrative of the embodiment shown by the drawings, my hotwell alarm system 10 comprises a housing or hotwell 12 formed with front and rear walls 14 and 16, end walls 18 and 20, a floor 22 and a roof 24, the roof 24 provided with a pair of hinged covers 26 and 28, each of which is secured to the front wall 14 by a latch 30, and can be lifted from closed position by means of the hand bar 32. As shown more particularly by FIG. 2, there is a water inlet line 34 leading into the hotwell 12 through end wall 20, and a water outlet line 36 secured in the floor 22 at the opposite end of the hotwell 12. The interior of the hotwell is partitioned by a series of parallel, spaced, baffles 38,40,42 and 44, forming "passes" 46,48, 50,52, and 54, the alternate baffles 40 and 44 extending from the floor 22 and open at their tops, and the alternate baffles 38 and 42 extending from the roof 24 and open at their bottoms, thereby to provide alternate passageway for the flow of water through the hotwell 12, as shown by the arrows.

The pass 46, between baffle 44 and end wall 18, is provided with a grid or strainer 56, supporting layers of filtering material 58, through which the water is filtered before reaching the outlet line 36. A window 60 is disposed in the front wall 14 of the hotwell 12, through which the passing water may be observed.

Coming now to the photoelectric circuit system, in the area of the pass 54 there is provided a glass-enclosed sealed lamp 62, connected to a source of current (not shown), which is mounted in the hotwell floor 22 so that its beam is directed to the roof 24 of the hotwell, while a photoelectric cell 64 is mounted in the cover 28 directly in the path of the beam from the lamp 62, with the water from the inlet line 34 flowing through said light beam. As shown more fully by FIG. 3, the photoelectric cell 64 forms part of an electrical circuit comprising an energy source 66, transformer 68, amplifier 70, alarm relays 72,72' buzzer 74 and signal lamp 76. There is also provided a stop buttom 78, by means of which the alarm can be turned off manually, and reset after an alarm has sounded. Such a photoelectric circuit is manufactured in Germany and known as the "Bega photoelectric switch 712", but similar circuitry capable of instantly detecting the slightest dimming of light from the lamp 62 can be substituted, as well.

OPERATION OF THE INVENTION

In the operation of my invention the circuitry is activated so that the light beam from the lamp 62 is directed to and in registry with the photoelectric cell 64. The normal flow of water through the hotwell 12 enters through inlet line 34 and proceeds under and over the baffles 38-44, as shown by the arrows, passes through the filtering material 58 and strainer 56 and enters the outlet line 36 from where it proceeds into the ship's boilers. The light from lamp 62 penetrates the clear water to reach the cell 64, thereby keeping the alarm circuit open. In the event, however, that any oil enters the hotwell through the inlet line 34 its progress will be impeded by the baffle 38 and will tend to rise to the surface, forming a film on the surface, thereby obstructing the light beam. The slightest dimming of this light will prevent its reaching the photoelectric cell 64, thereby causing it to activate the switch arm 80 to activate the alarm circuit, and the buzzer 74 to sound, and the signal lamp 76 to light up.thereby providing both visual and audible warning of the danger. This photoelectric alarm system is so sensitive that even a slight dimming of the light, caused by the presence of oil, will activate it in a matter of a very few seconds, so that no oil has an opportunity to reach the boilers by penetrating further into the system. As is obvious, the disposition of the baffles 38,40, 42 and 44, and the filtering means 56 and 58 serve to further impede the progress of incipient oil, to safeguard the boilers.

It is to be understood that the embodiment shown and described is by way of illustration and not of limitation, and that various changes may be made in the construction, composition and arrangement of parts without limitation upon or departure from the spirit and scope of the invention, or sacrificing any of the advantages thereof inherent therein, all of which are claimed.

Having described my invention, I claim:

1. A pollution detection device comprising an enclosed housing provided with a water inlet line at one end and a water outlet line at the other end, means within the housing to slow up the flow of water therethrough, a lamp disposed in the floor of the housing, with its light beam directed toward the roof of the housing, a photoelectric cell disposed in the roof of the housing in registry with the light beam, and an alarm circuit in engagement with the photoelectric cell, whereby a diminution of light from the lamp causes the photoelectric cell to activate the alarm.

2. A pollution detection device as claimed in claim 1, the means to slow up the flow of water through the housing comprising a series of parallel, spaced, solid baffles, alternately secured to the roof and the floor of the housing and forming passes causing the water to flow alternately under and over adjacent baffles.

3. A pollution detection device as claimed in claim 2, the lamp disposed in the floor of the housing adjacent the water inlet line.

4. A pollution detection device as claimed in claim 3, the alarm circuit including a buzzer device.

5. A pollution detection device a claimed in claim 3, the alarm circuit including a lamp.

6. A pollution detection device as claimed in claim 1, the housing being further provided with filtering means adapted to filter the water before it reaches the water outlet line.

7. A pollution detecting device as described in claim 6, the filtering means comprising a grid disposed within the housing before the water outlet line and filtering material supported by the grid.

8. A pollution detecting device as claimed in claim 2, the front wall of the housing being provided with a window adapted to permit visual inspection of the interior of the housing.

* * * * *